United States Patent [19]
Kutushov

[11] Patent Number: 5,980,479
[45] Date of Patent: Nov. 9, 1999

[54] METHOD AND SYSTEM FOR CORRECTING A BIOLOGICAL FLUID

[75] Inventor: Michael Kutushov, Petach Tikva, Israel

[73] Assignee: Idializa Ltd., Ramat Hasharon, Israel

[21] Appl. No.: 08/887,326

[22] Filed: Jul. 2, 1997

[51] Int. Cl.$^6$ .................................................. A61M 37/00
[52] U.S. Cl. .................................. 604/5; 604/4; 435/174; 436/806
[58] Field of Search ............................... 604/4–6, 8–10; 435/174; 436/806

[56] References Cited

U.S. PATENT DOCUMENTS

| | | | |
|---|---|---|---|
| 5,084,011 | 1/1992 | Grady | 604/24 |
| 5,123,901 | 6/1992 | Carew | 604/5 |
| 5,449,342 | 9/1995 | Hirose et al. | 604/4 |
| 5,510,716 | 4/1996 | Bufaloe, IV et al. | 324/445 |
| 5,536,475 | 7/1996 | Moubayed et al. | 422/101 |

OTHER PUBLICATIONS

Alexecvich et al., No. 1568313, (Feb. 1990).
Tazhudinovich et al., No. 1430, (Aug. 1994).
Alexeevich et al., No. 1537275, (Sep. 1989).

Primary Examiner—Corrine McDermott
Assistant Examiner—William Noggle
Attorney, Agent, or Firm—Browdy and Neimark

[57] ABSTRACT

A method and a system for correction a patient's biological fluid containing various low-, medium- and high-molecular toxins. The biological fluid substantially continuously flows through an extracorporeal flow line interconnected between an outlet and an inlet means attached to first and second locations, respectively, on a patient's body. A substantially small amount of the biological fluid containing various xenobiotics occupies the flow line at any given time as compared to a whole amount of the biological fluid contained in the patient's body. The biological fluid containing the various toxins is mixed with a predetermined amount of magneto-conductive particles capable of adsorbing the various toxins. An obtained mixture of the biological fluid with the particles passes through a magnetic field effect region and substantially all of the magneto-conductive particles are retained therein. Particle-free biological fluid is then returned into the patient's body through the inlet means.

59 Claims, 5 Drawing Sheets

METHOD AND SYSTEM FOR CORRECTING A BIOLOGICAL FLUID

FIELD OF THE INVENTION

The present invention relates to a method and a system for correction a biological fluid, such as blood, lymph, spinal cord fluid or the like.

BACKGROUND OF THE INVENTION

Methods of blood correction are known and widely used in particular for treatment of patients suffering from kidney and/or liver diseases. One of the conventional techniques, known as haemo- or lymph-perfusion, is based on passing the blood or lymph through an adsorbent such as granular activated carbon. Unfortunately, a relatively large amount of biological fluid, namely about 250–300 ml, is withdrawn from the patient's body at any given time and a duration of the whole process of purification is more than 2 hours. Actually, the carbon loses its effectiveness after 15–20 minutes from the beginning of the treatment because it slimes and, owing to the relatively large dimensions of the carbon particles, becomes formed with numerous channels which are formed therein by the blood during its passage therethrough. As a result, unpurified blood returns into the body.

Another conventional technique, known as haemodialysis, is based on the use of semipermeable membranes. Similarly to the haemoperfusion, this method also requires the withdrawal of about 400–600 ml of blood at any given time and more than 4 hours for the whole process of purification, wherein the blood passes through the apparatus typically more than 5 times. Both of the above described techniques disturb the blood's rheology. That is to say they traumatize the erythrocytes and thrombocytes. They also require bulky equipment.

Methods and devices for blood purification have been developed employing the so called haemoseparation technique which is based on the principles of magnetic separation. Generally, the magnetic separation procedure consists of retaining magnetic materials in a chamber disposed in a magnetic field. Systems of this kind typically provide mixing of the blood with a previously prepared magneto-conductive substance formed of paramagnetic beads having a coating which selectively binds a preselected pathogenic agent or endotoxin. Then, by passing a blood mixture containing the paramagnetic beads having the bound pathogenic agent through a magnetic field, the paramagnetic beads are magnetically separated from the blood.

U.S. Pat. No. 5,123,901 discloses a method and an apparatus for removing preselected cells or viruses from the blood. The blood is first tested for selection a preselected pathogenic agent and identifying an associated antigenic agent. A composition is then prepared, such as an immunoglobulin or an antibody, for coating a plurality of paramagnetic beads with outer layers so as to recognize and bind selectively to the preselected pathogenic agent. The paramagnetic beads have a smooth surface in order to minimize the amount of antibody necessary to coat the beads. The blood is perfused into a flow line and the coated paramagnetic beads are metered into the blood either before entering by the latter a mixing coil, or thereafter. A received mixture of blood and paramagnetic beads/pathogenic agent complexes flows into a chamber of a magnetic separator. A graded magnetic field is provided along the length of the separation chamber so as to adhere substantially all of the paramagnetic beads/pathogenic agent complexes to the separation chamber wall. However, both the mixing chamber and the separation chamber are bulky, namely each about 300 cm in length. About 600 to 700 ml of blood occupies the flow circuit at any given time, while the purging process is completed in approximately 6 to 10 hours of operation. Additionally, the magnetic field is graded such that it begins at 4,000 Gauss (0.4 T) and increases to about 10,000 Gauss (1 T), which is too much for such a biological fluid as blood. Indeed, it is known in the art that the magnetic field intensity which is suitable for intervention into a biological fluid is defined by the properties of the latter. This is more essential for such a multicomponent biological fluid as blood containing crythrocytes whose equidistance increases and membrane resistivity decreases with the increase of the magnetic field. As a result, the erythro-cytes grow old and break.

PCT Publication No. WO 94/21310 discloses a method and an apparatus for correcting a biological fluid typically based on mixing the latter with a biocompatible suspension of a magneto-conductive composition within a mixing chamber and, then, passing the obtained mixture through a filter disposed within a magnetic field. The biological fluid is corrected in a number of cycles. In order to provide more effective mixing, the mixing chamber is filled in with discrete doses of the biological fluid and the suspension of the magneto-conductive composition. The obtained mixture is left standing whilst being continuously mixed, and, then, each further dose is added to the previously obtained mixture. Then, the resulting mixture passes through a filter disposed in a magnetic field effect region. The time of passage of the mixture through the filter is preset so as to achieve an optimum effect in the magnetic field which does not exceed 120 mT. Unfortunately, such procedure is slow, requiring that about 100 ml of the biological fluid be withdrawn from the body during a cycle and resulting in about 10 hours of operation for complete correction of the whole amount of the patient's blood.

It should be noted that such parameters as the amount of biological fluid which is withdrawn from the patient's body at any given time and the duration of the whole treatment are very important and even determinant when dealing with endotoxic and/or exotoxic shocks which are usually caused by poisoning.

SUMMARY OF THE INVENTION

It is a broad object of the present invention to overcome the above listed and other disadvantages of the conventional systems of the kind and provide a method and a system for correcting a patient's biological fluid based on a unique combination of adsorbing various endotoxins and exotoxins by a plurality of paramagnetic particles and separation thereof by a magnetic field.

It is a further object of the invention that the method and system for correcting the biological fluid do not influence the properties of the biological fluid, and, therefore, the organism haemodynamics are not affected.

There is thus provided according to a broad aspect of the present invention a system for correcting a patient's biological fluid containing various low-, medium- and high-molecular toxins, the system comprising:

(i) outlet means for attaching to a first location on a patient's body for substantially continuously withdrawing therefrom the biological fluid containing the various toxins;

(ii) an extracorporeal flow line coupled to said outlet means for passing therethrough, in a substantially continuous flow, a predetermined substantially small amount of the biological fluid as compared to a whole amount of the biological fluid contained in the patient's body, so as to be mixed with a plurality of magneto-conductive particles capable of adsorbing said toxins for obtaining a mixture thereof;

(iii) magnetic means for providing a magnetic field region within a flow of said mixture for retaining said magneto-conductive particles in said region from a flow of particles-free biological fluid, said magnetic field having substantially low intensity and substantially high gradient and magnetic flux density within said region;

(iv) inlet means for attaching to a second location on the patient's body for returning the particles-free biological fluid back into the patient's body; and (v) control means coupled to the flow line and to the magnetic means for operation thereof.

Preferably, the flow line is in the form of a flexible tube. The magneto-conductive particles may be contained in a vessel coupled to the flow line through a pipe. To this end, the system comprises a feeding means for substantially continuously feeding the particles into and through the flow line. Preferably, the feeding means comprises a pump coupled to the vessel for supplying air thereto so as to provide an excessive pressure within the vessel. Additionally, the system may comprise a feeding means for substantially continuously feeding the biological fluid containing various toxins into and through the flow line. A peristaltic pump may be employed for feeding both the magneto-conductive particles and the biological fluid.

Alternatively, the magneto-conductive particles may be located inside the flow line in a flow path of the biological fluid containing the various toxins. The flow line may include first and second flexible tubes and a sealed vessel. The magneto-conductive particles are accommodated within a bottom region of the vessel. The first tube is connected between the outlet means and the particles, while the second tube is connected between the inlet means and a top region of the vessel.

Preferably, the particles are contained in a suspension thereof. The suspension may be formed of either a blood substitute composition, or physiological solution or the like allowed for intravenous injection.

The biological fluid which can be corrected by the system may be the patient's blood, or lymph, or spinal cord fluid. The small amount of the biological fluid which occupies flow line at any given time is within the range 15–50 ml. If the biological fluid is blood, the first and second locations may be associated with the patient's artery and vein, or with two locations on his vein. If the biological fluid to be corrected is the patient's lymph, the first and second locations are associated with the patient's large pectoral lymph duct and vein. If the biological fluid to be corrected is the patient's spinal cord fluid the first and second locations are associated with the spinal cord channel.

The magneto-conductive particles are formed of paramagnetic or ferromagnetic material, and may have prevailing hydrophilic or hydrophobic properties.

The system, preferably, also comprises a mixing means located in the flow path of the biological fluid containing the various toxins. The mixing means may comprise a multi-threaded worm mechanism. Alternatively, the mixing means may comprise a magnetic mechanism having displaceable opposite magnetic poles.

Preferably, the magnetic means comprises a generating means for generating the magnetic field and adhering moans for adhering thereon the magneto-conductive particles, wherein the adhering means are accommodated inside the flow line. The generating means may include at least one permanent magnet mounted outside the flow line and proximate thereto. The permanent magnet may be in the form of either a substantially flat plate or a ring surrounding the flow line. Opposite poles of each magnet may be connected by a cover plate formed of a magnetic soft material. The adhering means preferably includes a paramagnetic or ferromagnetic filler element installed inside the flow line within the magnetic field effect region. The filler may be in the form of a loosely laid wire, preferably, barbed wire. The wire, preferably, has a varying diameter and a varying laying density within the magnetic field effect region. Alternatively, the generating means and the adhering means may be constituted by at least one permanent magnet accommodated inside the flow line.

The control means may include a plurality of clamps accommodated along the flow line for regulating the flow of the biological fluid and a monitoring means for checking velocities of the flow of the biological fluid containing the various toxins, the mixture and the particle-free biological fluid.

Preferably, there is also provided a filtering means for removing water from blood which may include at least one semipermeable membrane, or water adsorbent material formed of hydrolyzed starch polymer. The filtering means may be accommodated in the flow path of either the biological fluid containing the various toxins, or the particle-force biological fluid.

The magneto-conductive particles are formed with activated porous surfaces. The particles may be formed of iron, iron oxide, carbon coated iron, silicone coated iron, aluminum coated iron, dextran coated iron. Preferably, the magneto-conductive particles are further coated with a protective layer formed of protein or the patient's blood.

There is also provided a method of correcting a patients biological fluid containing various low-, medium- and high-molecular toxins during a flow thereof through an extracorporeal flow line interconnected between an outlet and an inlet means attached to first and second locations, respectively, on the patient's body, comprising the steps of:

(a) withdrawing at any given time a substantially small amount of the biological fluid containing various toxins from the patient's body through said outlet means and substantially continuously feeding thereof into the flow line so as to be mixed with a predetermined amount of magneto-conductive particles for adsorbing the toxins and obtaining a mixture thereof; and (b) providing a magnetic field effect region in a flow path of the obtained mixture for passing the mixture therethrough and retaining substantially all of the magneto-conductive particles in said region.

More specifically, the present invention is used for correcting the blood and is, therefore, described below with respect to this application.

BRIEF DESCRIPTION OF THE DRAWINGS

In order to understand the invention and to see how the same may be carried out in practice, preferred embodiments will now be described, by way of example only, with reference to the accompanying drawings, in which:

FIG. 4b schematically illustrates the principles of operation of a magnetic means suitable for the separation assembly of FIG. 4a;

DETAILED DESCRIPTION OF THE PREFERRED EMBODIMENTS

Figure 1:
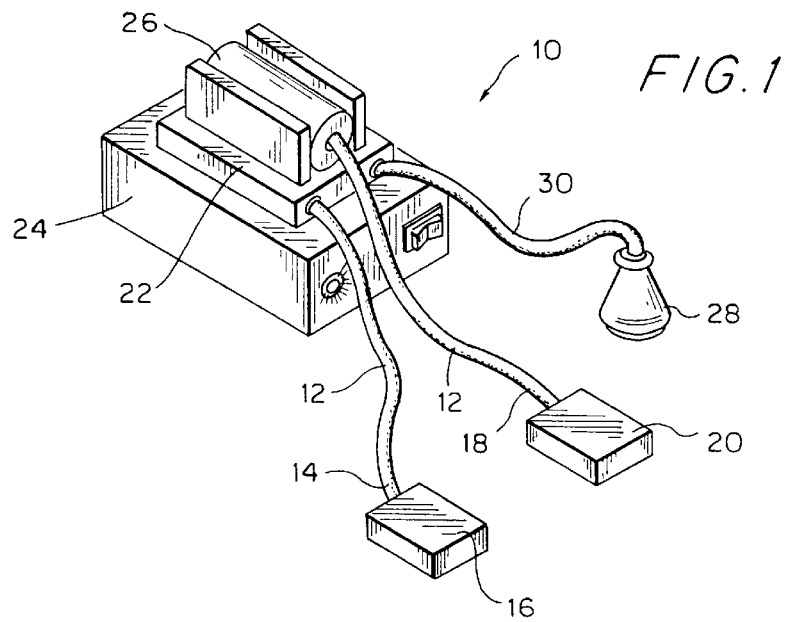
FIG. 1 is a pictorial illustration of the principal components of a system according to the invention.

Referring to FIG. 1 there is illustrated an extracorporeal system, generally designated 10, associated with a patient (not shown) for correcting his/her blood by removing therefrom various toxins. The system 10 comprises a flow line in the form of a silicon, or polychlorvinyl, tube 12. The tube 12 is coupled at its' one end 14 to a conventional outlet port 16 for withdrawing the blood from a patient's vein. An opposite end 18 of the tube 12 is coupled to a conventional inlet port 20 for returning the blood into the patient's vein. A peristaltic pump 22 is coupled to a motor 24 and conventionally operated by the latter for providing a substantially continuous flow of the blood to and through the tube 12. The peristaltic pump 22 is a known device which is widely used and, therefore, its construction and operation need not be specifically described. The system 10 is further provided with a separation assembly, generally designated 26, which is installed in the tube 12 so as to be in a flow path of the blood. The construction and operation of the separation assembly 26 will be described more specifically further below with reference to FIGS. 4a and 4b. Further provided is a vessel 28 containing a biocompatible magneto-conductive material (not shown). The vessel 28 is coupled through a pipe 30 to the tube 12. The same pump 22 is used for substantially continuously feeding the magneto-conductive material from the vessel 28 into the tube 12.

The biocompatible magneto-conductive material is in the form of paramagnetic or ferromagnetic particles suspended within a liquid solution formed of any suitable blood substitute composition or the like allowed for intravenous injection, such as for example gelatin, or blood plasma, or physiological solution. The particles are formed of one of the following materials: iron in its reduced form, so-called 'ferrum reductum'; iron oxide; carbon coated iron; dextran coated iron, silicone coated iron, aluminum coated iron. Dispersed powders of 'ferrum reductum', iron oxide and carbon coated iron are obtainable either commercially, or by any suitable known technique. The aluminum and silicone coated iron particles may be obtained by the known plasma-chemical process, while the dextran coated iron particles - by the known technique of ultrasonic binding. The particles of either kind are, then, specifically processed so as to have swelled, activated surfaces for possessing the following properties:

1) high adsorption capability due to their porous, irregular surface, rather than smooth, so as to provide a total porosity up to 2 $cm^3/g$ for being capable of adsorbing low-, medium- and high-molecular toxins contained in the biological fluid;

2) a specific surface area (per weight) of the whole magneto-conductive material up to 900 $m^2/g$;

3) bulk weight of the particles characterizing their density is from 0.3 to 1.0 $g/cm^3$.

Moreover, the particle is of substantially small size about 0.01 μm to 1 mm in diameter and its magnetization value is about 130 to 200 emu/g so as to be retained by a magnetic field due to its ponderomotive forces. The particles are bioinert to the biological fluid, i.e. non-toxic and non-corrosive. It is known in the art of adsorbing materials that density, total porousness and, therefore, total surface area are the most important factors defining efficiency of the adsorbing process. To this end, for example, maximum values of the total porousness and specific surface area of activated carbon used in the conventional haemo- or lymph-perfusion technique are about 1.11 $cm^3/g$ and 650 $m^2/g$, respectively.

Optionally, the particles may be further coated by a protective coating formed of either protein of any known kind, particularly a food protein, or the patient's blood, so-called 'auto-blood'. Alternatively, or additionally, the particles may be coated by a selective coating, for example antibody, depending on a preselected pathogenic agent to be removed from the biological fluid. Moreover, the paramagnetic particle either coated or not may be further modified by antibiotics or similar medical compounds.

The process of preparation of such magneto-conductive material, namely the coated and non-coated paramagnetic particles and the suspension thereof, is disclosed in a copending application which is assigned to the assignee of the present application. It should be noted that the provision of the suspension of the paramagnetic particles is optional solely for facilitating a flow of such particles through the flow line. The suspension may contain from 0.5 to 90% of the paramagnetic particles.

It should also be noted that if such an extracorporeal system for correcting a patient's blood is interconnected between the patient's artery and vein, there is no need for any pump means and, therefore, for any motor. The patient's blood is fed into and passes through the tube 12 due to a typically existing pressure difference between the artery and the vein. The blood thus flows through the flow line with its usual velocity of circulation within the patient's body which is about 100–120 ml/min.

Figure 2:
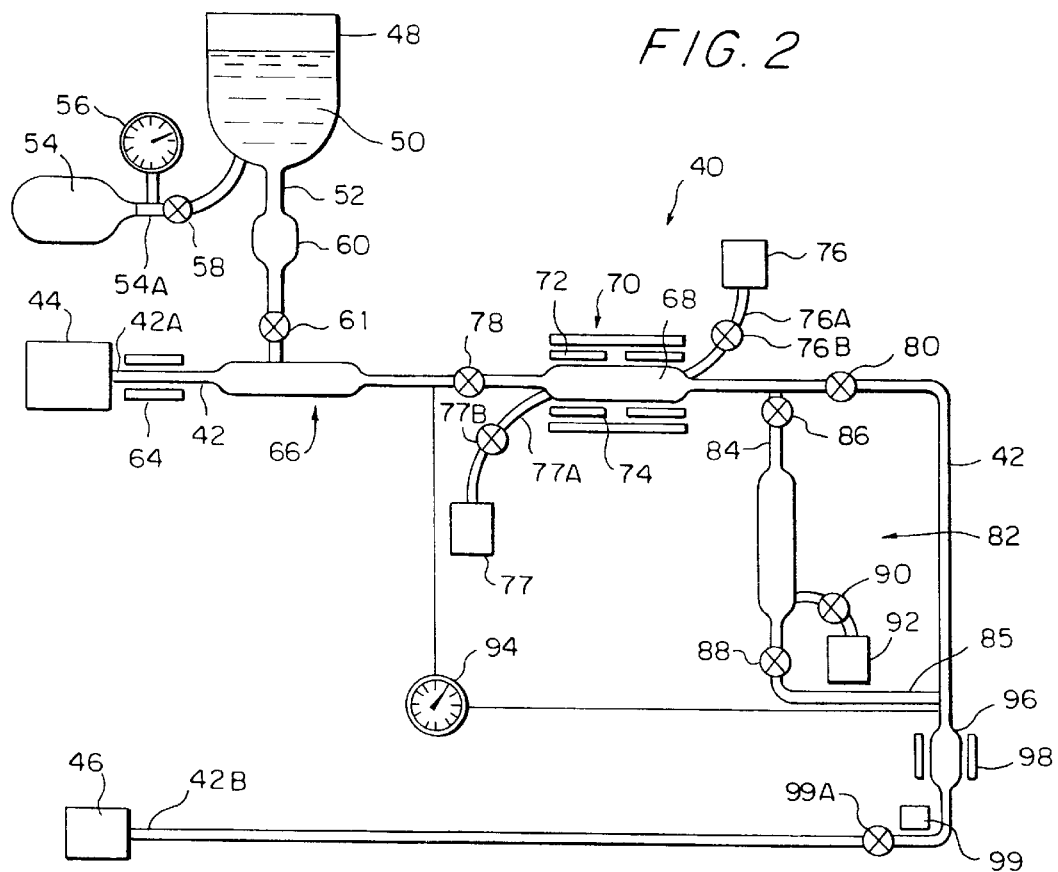
FIG. 2 is a schematic block diagram illustrating the main components of a system according to one embodiment of the invention.

Referring to FIG. 2 there is illustrated an extracorporeal system, generally denoted 40, for correcting the blood circulating between a patient's artery and vein. The system 40 similarly comprises a tube 42 connected at its opposite ends 42a and 42b to outlet and inlet ports 44 and 46 which are attached to the patient's artery and vein, respectively. A vessel 48 containing a biocompatible suspension of a magneto-conductive material 50 is coupled to the tube 42 through a pipe 52. A small pear-like pump 54 is connected to the vessel 48 through a pipe 54a for feeding air in a manner to provide an excessive pressure within the vessel 48. This results in continuous supply of the suspension 50 into the tube 42. As shown, the air supply is controlled and regulated by a manometer 56 and a clamp 58. The flow of the suspension 50 into the tube 42 is, in turn, visually controlled and regulated by means of conventional dropper 60 and clamp 61 which are installed in the pipe 52. Further provided is an electromagnet 64 mounted proximate to the outlet port 44, the purpose of which will be described further below. A mixing assembly 66 is optionally provided inside the tube 42 so as to be in the flow path of the blood and of the suspension 50 for obtaining a mixture containing paramagnetic particles which have captured toxins, and paramagnetic particles which may free of toxins and the blood free of particles. The construction and operation of the mixing assembly 66 will be described further below with reference to FIG. 3.

The system 40 further comprises a separation assembly 68 having a magnetic mechanism 70. The separation assembly 68 is installed in the tube 42 downstream of the mixing assembly 66 so as to be in the flow path of the obtained mixture. The magnetic mechanism 70 includes a pair of spaced, parallel, horseshoe, permanent magnets 72 and 74 enclosing the assembly 68 for providing a magnetic field region thereinside and retaining the particles within that region. The construction and operation of the separation assembly 68 will be described more specifically further below with reference to FIGS. 4a and 4b. A conventional injector 76 and a vessel 77 are coupled to the tube 42 through a pair of pipes 76a and 77a and a pair of clamps 76b and 77b, respectively, for cleaning the separation device 68 after use so as to remove therefrom the particles retained by the magnetic field. To this end, a pair of clamps 78 and 80 are coupled to the tube 42 upstream and downstream of the assembly 68, respectively, so as to selectively connect and disconnect the latter from the flow line. It will be readily understood that the magnetic mechanism 70 is taken away from a vicinity of the separation assembly 68 for several seconds during the process of cleaning.

A conventional filtering device, generally designated 82 for removing water from the blood, is optionally provided. As shown, the device 82 is coupled to the tube 42 through a pair of pipes 84 and 85 so as to be disposed in the flow path of the blood ensuing from the separation assembly 68. A pair of clamps 86 and 88 are mounted on the pipes 84 and 85 and operated in a manner to selectively direct the blood into the filtering device 82. The operation of the device 82 is based on the principles of ultrafiltration consisting in that the blood, under an excessive pressure, passes through a plurality of parallel, tube-shaped, semipermeable membranes (not shown) extending along the flow path of the blood. Thus, the blood, which is more viscous than water by approximately 5 times, passes along the membranes thereinside, while the water penetrates through the membranes. This technique is known per se and, therefore, need not be specifically described. To this end, additional clamp 90 and vessel 92 are provided for gathering the separated water. Alternatively, although not specifically shown, the filtering device 82 may be accommodated upstream of the mixing assembly 66 so as to be in the flow path of the blood before it is mixed with the magneto-conductive material 50. It should be noted that the ultrafiltration may be replaced by another well known technique based on the use of water suitable adsorbent such as, for example, copolymer of hydrolyzed starch with polyakryl-nitryl.

As further shown in FIG. 2, coupled to the tube 42 is an additional manometer 94 for controlling the velocities of both the mixture before entering the separation assembly 68 and the blood ensuing therefrom. Installed in the tube 42 downstream of the separation assembly 68 is a trapper 96 comprising a magnetic mechanism 98, the purpose of which will be described further below. A sensor 99, either ultrasonic or optical, is mounted proximate to the tube 42 downstream of the trapper 96. The sensor 99 is capable of detecting the existence of any magnetic material in the blood ensuing from the trapper 96. For the purpose, an additional clamp 99a is provided and operated by the sensor 99 for shutting off the passage of the blood towards the inlet port 46, upon detecting the existence of the magnetic material in the blood.

Figure 3:
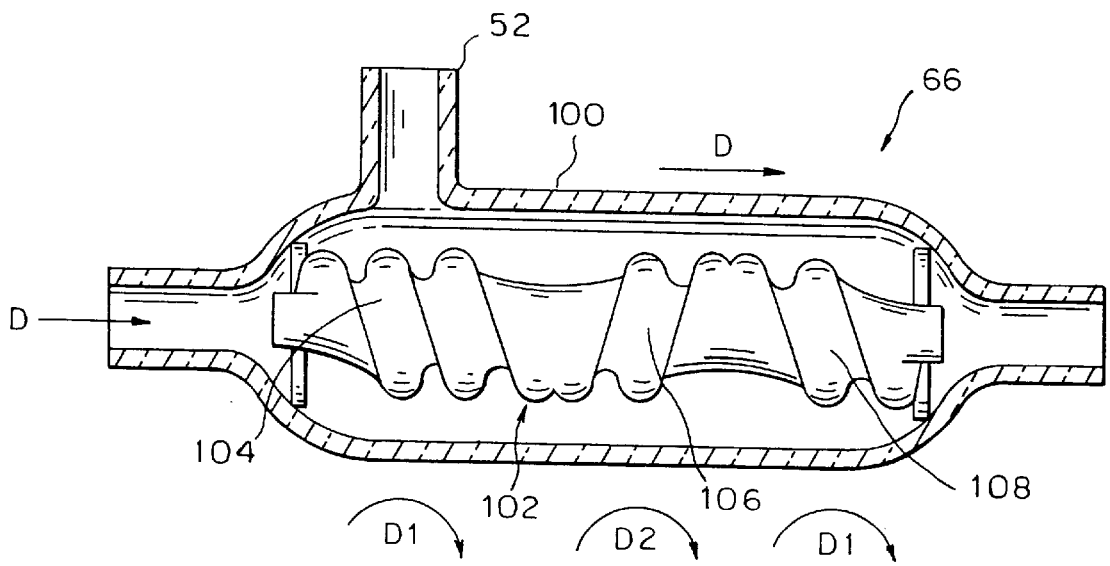
FIG. 3 is an exploded, partly cross-sectional view illustrating a mixing assembly suitable for the system of FIG. 2.

Turning now to FIG. 3, the mixing assembly 66 is optionally formed of a slightly thickened portion 100 of the tube 42. A three-threaded worm mechanism 102 is mounted inside the portion 100. The mechanism 102 includes three worm elements 104, 106 and 108 which are either formed integrally or axially coupled. It will be readily understood that such construction of the worm mechanism 102 provides sequential rotation of the flow of blood together with the suspension 50 in a direction $D_1$, in an opposite direction $D_2$ and, then, again in the direction $D_1$ during a progressive movement of the blood and the suspension through the portion 100 in a flow direction D. Thus, a mixture containing the blood and adsorptive and non-adsorptive paramagnetic particles is provided without interrupting the continuous flow of the mixture. Obviously, such a multi-threaded mechanism 102 may comprise more than three worm elements.

Figure 4A:
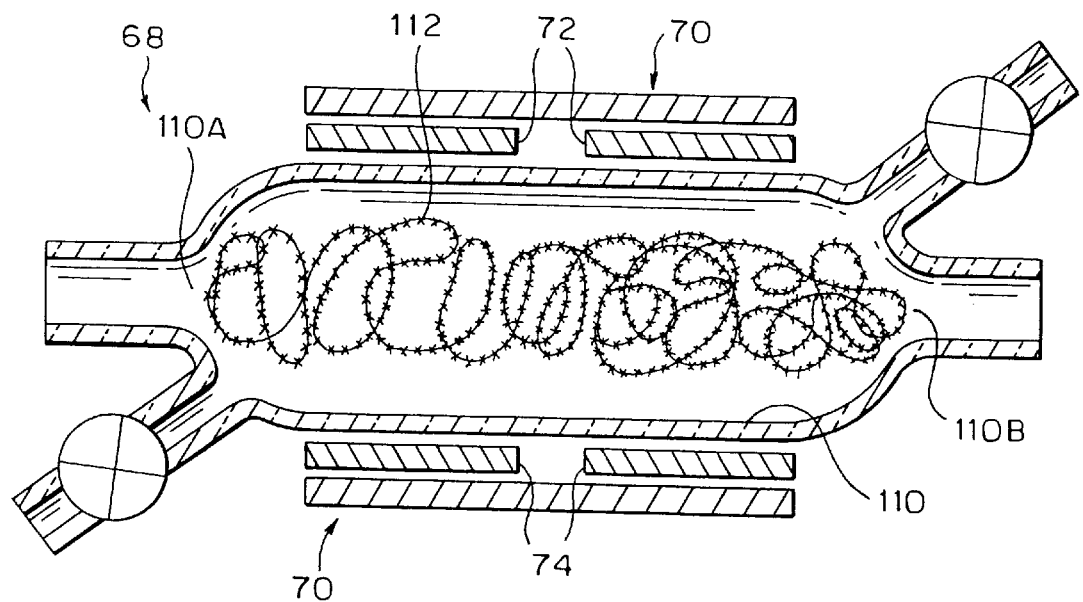
FIG. 4a is an exploded, partly cross-sectional illustration of a separation assembly suitable for the system of FIG. 2.

Reference is now made to FIG. 4a illustrating the separation assembly 68. Optionally, the separation assembly 68 is in the form of slightly thickened portion 110 of the tube 42. The portion 110 has its front and rear ends 110a and 110b, respectively, and is approximately of 20 mm in its inner center diameter. A barbed wire 112 is accommodated in the portion 110 in such a manner that a total volume of the wire is approximately 10–50% of the volume of the portion 110. The wire 112 is made of a paramagnetic or ferromagnetic material such as, for example, permendur. As clearly shown, the wire 112 is loosely laid inside the portion 110 in such a manner that its laying density at the front end 110a of the portion 110 is less than that of the rear end 110b. Additionally, although not specifically shown, a diameter of the wire 112 decreases from approximately 0.5 mm at the front end 110a to approximately 0.05 mm at the rear end 110b of the portion 110. The wire 112 is coated with a bioinert material (not shown) such as, for example, silicone.

Figure 4B:
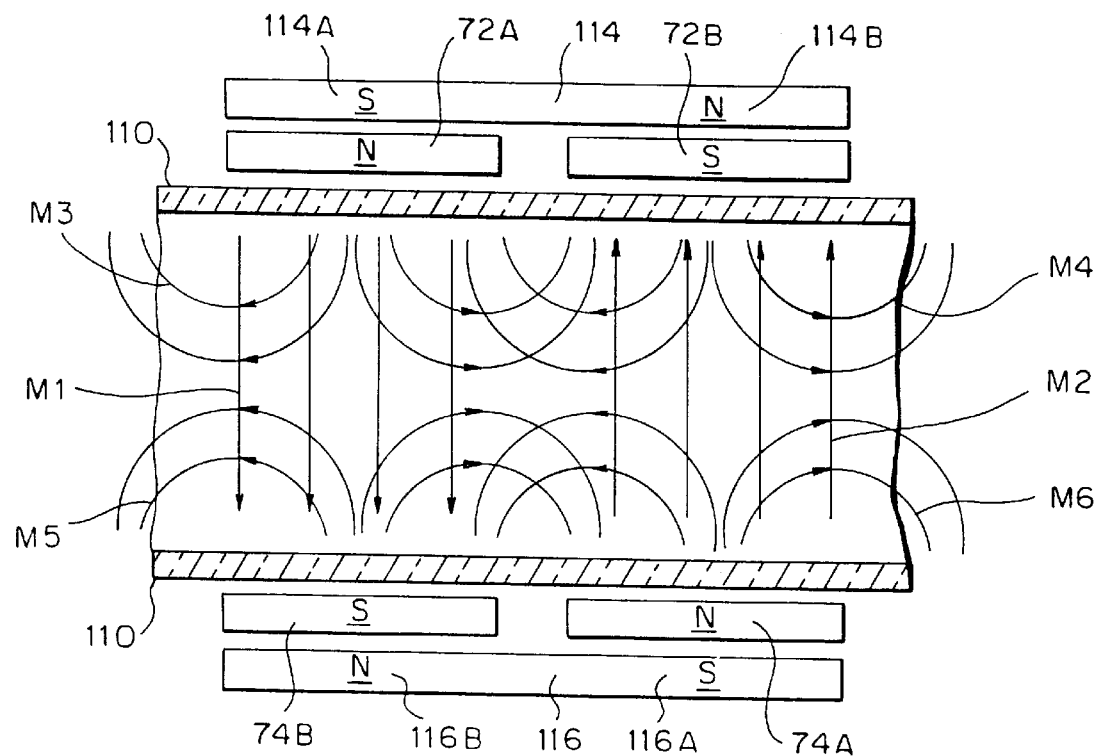

Referring to FIG. 4b, the magnets 72 and 74 are disposed in such a manner that north and south poles 72a and 72b of the magnet 72 oppose south and north poles 74b and 74a of the magnet 74, respectively. The poles 72a and 74b provides a magnetic field direction $M_1$, while the poles 72b and 74a provide a magnetic field of an opposite direction $M_2$. The opposite poles of the magnets are coupled by a pair of metal plates 114 and 116, respectively, formed of a magnetic soft material such as, for example, steel. It will be readily understood that additional magnetic poles 114a–114b and 116a–116b are, therefore, formed in the plates 114 and 116 which generate magnetic fields directions $M_3$, $M_4$, $M_5$ and $M_6$ inside the portion 110.

Thus, owing to the provision of the plates 114 and 116 a flux density of the total magnetic field inside the portion 110 increases. Furthermore, on the one hand, such a paramagnetic wire 112 provides a high gradient of the magnetic field in a direction transverse to the flow direction D inside the portion 110. On the other hand, such a varying diameter of the wire 112 provides a high gradient of the magnetic field along the flow direction D. The wire 112 itself constitutes a physical retainer for preventing the paramagnetic particles from flowing out of the portion 110. The provision of such a varying laying density of the wire 112 as described above enables to obtain an even distribution of retained particles so as not to impede the flow of the mixture through the portion 110. Moreover, the provision of such a barbed wire enables to the gradient of the magnetic field inside the portion 110 to be further increased. As a result, a relatively weak magnetic field of about 30 mT to 100 mT is effective enough for separating substantially all of the paramagnetic particles from the blood containing them.

Alternatively, although not specifically shown, at least one permanent magnet, which is preferably planar, may be installed inside the portion 110 serving, thereby, for both generating the magnetic field and retaining the paramagnetic particles adhering on the magnet. Additionally, each of the horseshoe magnets 72 and 74 may be replaced by one or more flat- or ring-shaped permanent magnets.

Figure 5:
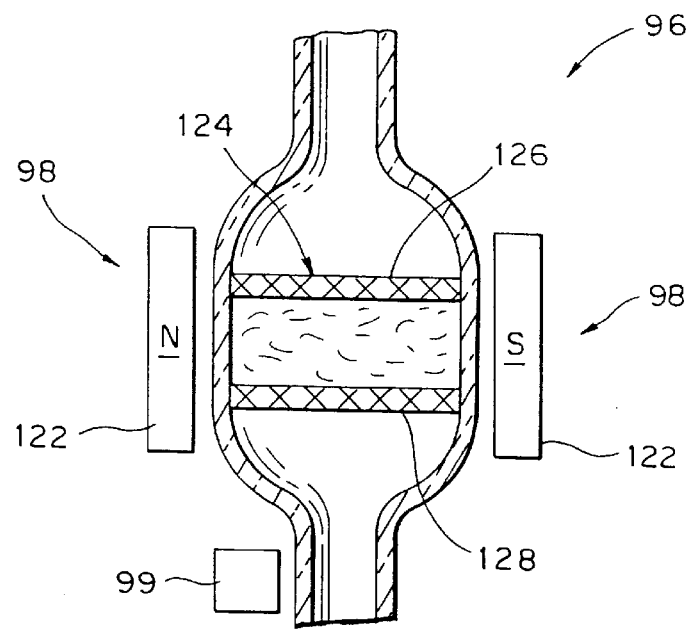
FIG. 5 is an exploded, partly cross-sectional illustration of a trapper suitable for the system of FIG. 2.

Turning now to FIG. 5, the trapper 96 is optionally formed of a slightly thickened portion 120 of the tube 42. The magnetic mechanism 98 comprises a permanent magnet 122, for example horseshoe, mounted proximate to the portion 120 in a manner to enclose the latter between its opposite poles. A filler element, generally designated 124, is installed inside the portion 120. The element 124 includes a pair of spaced parallel lattices 126 and 128, the space between the lattices being filled in by particles formed of activated carbon. Alternatively, the filler element 124 may be designed like a single lattice, or a wire formed of paramagnetic or ferromagnetic material, for example such as the wire 112. Thus, the magnet 122 provides a magnetic field region within the portion 120.

The system 40 operates in the following manner. Approximately 15–50 ml of blood, containing various xenobiotics, i.e. low-, medium- and high-molecular toxins, is withdrawn from the patient's artery and directed into the flow tube 42 through the port 44. A suitable anticoagulant such as, for example, heparin of approximately 500–900 units per kilogram depending on the patients weight, is introduced into the blood either intravenously, prior to the withdrawal, or into the system 40. The blood first passes between the poles of the electromagnet 64 which generates an impulsive magnetic field having intensity of about 30–50 mT. Such a magnetic field provides a so-called 'shaking effect' for liberalization of the toxins contained in the blood, namely tearing off those toxins while been have been adsorbed by the blood proteins. This increases the efficiency of the whole process of separation by 15–20%.

The blood then continues its flow into the portion 100 of the mixing assembly 66. Concurrently, the suspension 50 containing from 2 to 50% of the paramagnetic particles continuously flows into the portion 100 with a velocity of about 5–20 ml/min. The blood and the suspension 50 during their progressive flow in the direction D are together sequentially rotated in opposite directions and are, therefore, mixed. During the rotation, at least a part of the paramagnetic particles due to their swelled, activated surfaces adsorb the toxins contained in the blood, thus obtaining a mixture containing the adsorptive and non-adsorptive paramagnetic particles and particle-free blood. The mixture enters the portion 110 and passes through the magnetic field region between the magnets 72 and 74. As a result, the adsorptive and non-adsorptive particles adhere to the wire 112 and the particle-free blood ensues from the portion 110. The particle-free blood continues its flow in the direction D through the filtering device 82, wherein water is removed therefrom in the above described manner. Thereafter, water and particle-free blood enters the portion 120 of the trapper 96, wherein it again passes the magnetic field generated by the magnet 98. If there occasionally exist paramagnetic particles, either adsorptive or non-adsorptive, they are retained by the filler element 124. Then, the blood ensuing from the portion 120 flows towards the inlet port 46 for returning into the patient's vein. If the sensor 99 accommodated as described above detects an existence of any magnetic material within the blood, it immediately operates the clamp 99a for interrupting the blood flow into the patient's body.

Additionally, it is known that the passage of the blood through the magnetic field increases the activity of acetylholynesteraz. The whole process of correction of 5–6 liters of the patient's blood is completed in about 0.5–1.5 hours using about 50–500 ml of the suspension.

Figure 6:
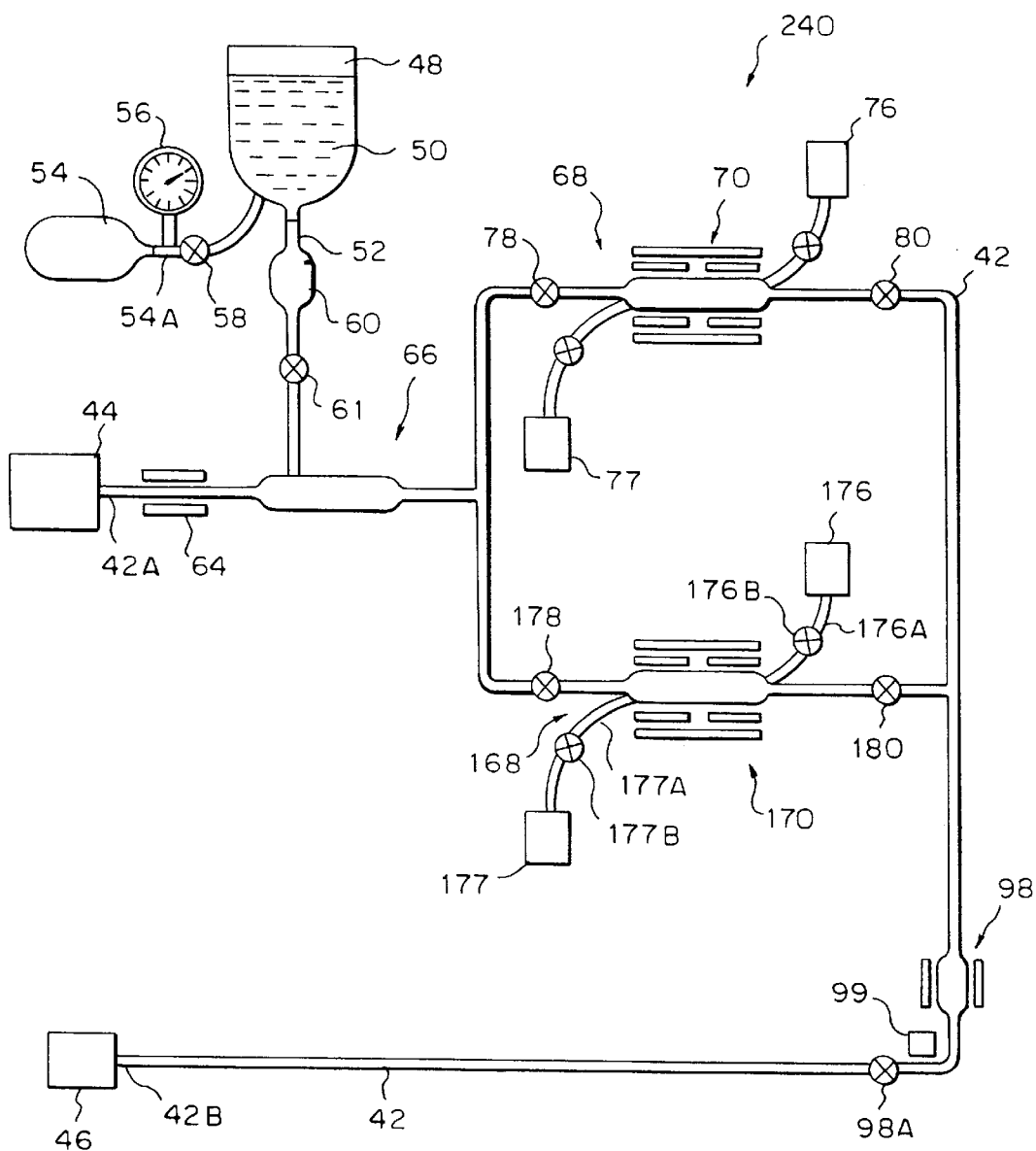
FIGS. 6, to 8 are schematic block diagrams illustrating the main components of three systems constructed and operated according to three more embodiments of the invention, respectively.

Reference is now made to FIG. 6 illustrating a system 140 according to another embodiment of the invention. The same reference numbers are used for indicating those constructional parts which are common to both the systems 40 and 140. The system 140 differs from the previously described system 40 in the provision of an additional separation assembly, generally designated 168. The assembly 168 is constructed and operative similar to the assembly 68 and comprises a magnetic mechanism 170 which is similar to that of the mechanism 70. The assembly 168 is connected through pipes 176a and 177a to injector 176 and vessel 177, respectively, which are put into operation for cleaning thereof after use. For the purpose, a pair of clamps 176b and 177b is mounted on the pipes 176a and 177a. The assemblies 68 and 168 are accommodated in such a manner that the flow of the mixture ensuing from the mixing assembly 66 may be selectively directed into either separation assemblies 68 or 168. To this end, an additional pair of clamps 178 and 180 is provided. It will be readily understood that, during the operation of the separation assembly 68, the assembly 168 may be cleaned, and vice versa. This results in a non-interruptive process of correction.

Figure 7:
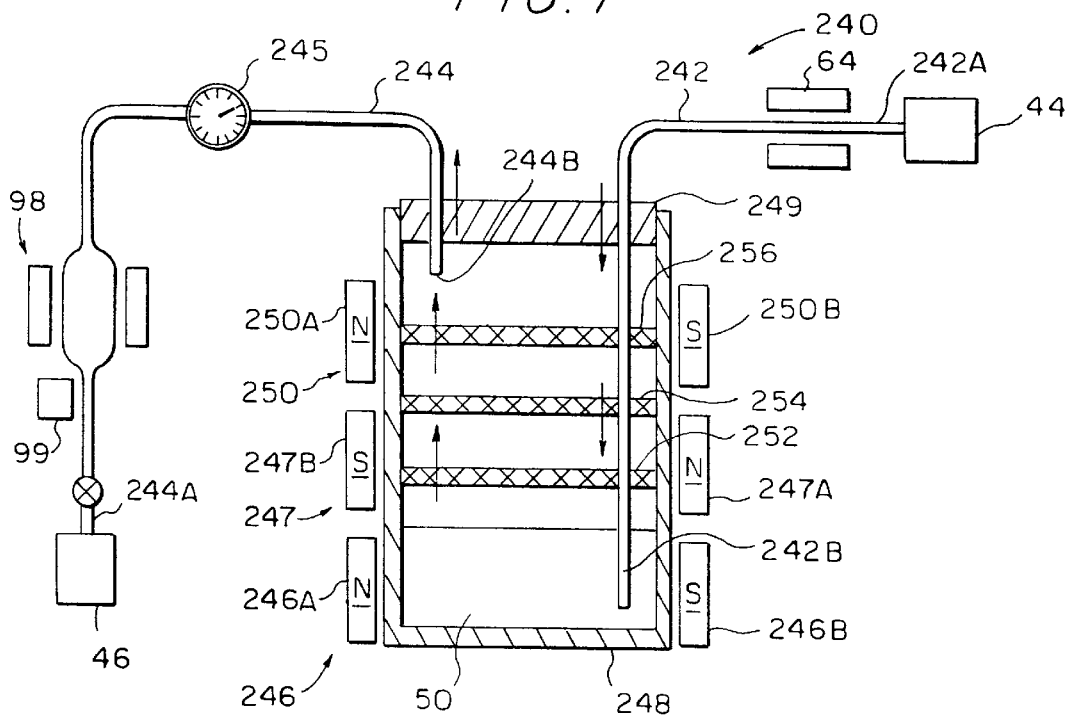

FIG. 7 illustrates a system, generally designated 240, constructed according to still another embodiment of the present invention. Similarly, in order to facilitate understanding, the same reference numbers indicate the common constructional parts of the systems 40, 140 and 240. The system 240 differs from the previously described systems 40, 140 in that there is no flow of the suspension of the magneto-conductive material 50 into the flow line. Both the mixing and the separation are carried out within a vessel 248 containing the biocompatible suspension 50 disposed within a bottom region thereof. The vessel 248 is closed by a scaled cover 249. Additionally, the tube 42 of the system 40 is replaced by a pair of separate tubes 242 and 244. The tube 242 is connected at its one end 242a to the outlet port 44 attached to the patient's artery, while the tube 244 is coupled at its one end 244a to the inlet port 46 attached to the patient's vein. Free ends 242b and 244b of the tubes 242 and 244, respectively, are inserted into the vessel 248 through a pair of openings (not shown) provided in the cover 249. The end 242b is dipped into the suspension 50, while the end 244b is spaced therefrom.

It is appreciated that the blood containing various xenobiotics passes through the tube 242 and, upon ensuing therefrom through the end 242b, passes through the suspension 50 and then enters the end 244b of the tube 244. Three magnets 246, 247 and 250 are aligned in a spaced parallel relationship along a length of the vessel 248 so as to enclose the latter between their opposite poles 246a–246b, 247a–247b and 250a–250b. Three spaced parallel filler elements 252, 254 and 256 formed of paramagnetic or ferromagnetic material are aligned along the vessel 248 thereinside. Each of the filler elements is in the form of a lattice, or loosely laid material. The lowermost magnet 246 is continuously or periodically rotated so as to 'shake up' the suspension 50 and, thereby, provide a movement of the paramagnetic particles within the bottom region of the vessel 248 for improving a mixing of the particles with the blood and, therefore, the adsorbing process. Thus, a mixture containing the adsorptive and non-adsorptive particles and the particle-free blood is provided. Subsequent passage of the mixture through the filler elements 252, 254 and 256 results in substantially all of the particles adhering to the elements 252–256. The particle-free blood then enters the tube 244 and passes through the trapper 96 in the manner described above in respect of the system 40.

Figure 8:
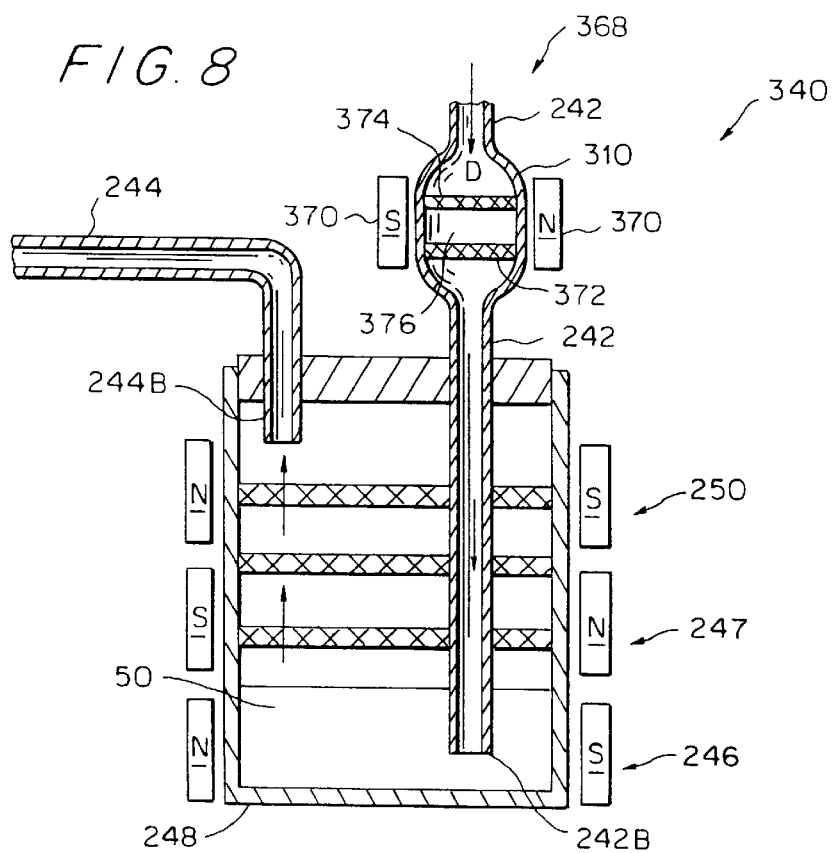

Turning now to FIG. 8, a system, generally designated 340, is illustrated. The system 340 is generally similar to the system 240 and additionally comprises a separation assembly 368 which is accommodated in the tube 242 upstream of the vessel 248. As shown, the assembly 368 is optionally formed of a thickened portion 310 of the tube 242 and enclosed by opposite poles of a permanent magnet 370. The magnet 370 may be either horseshoe or ring-shaped. Obviously, more magnets may be used being located in a spaced parallel relationship along a length of the portion 310 outside thereof. A pair of spaced parallel lattices 372 and 374 are mounted inside the portion 310 extending transverse to the flow direction D. Enclosed between the lattices is a magneto-conductive material 376 formed of paramagnetic or ferromagnetic particles with prevailing properties of hydrophobic colloid, rather than hydrophilic, while the particles 50 are, on the contrary, of prevailing hydrophilic properties. Hence, the material 376 is capable of adsorbing another kind of toxins such as, for example, bilirubin, holysterin or other poly-unsaturated fatty acids, which cannot be captured by hydrophilic adsorbents.

In order to further describe the present invention, the following table is provided. It is to be understood that the system has been tested by correcting the biological fluid of laboratory animals, blood substitutes or donor blood. Data included in the table illustrates efficiency of the above described process of correction of one liter of the donor blood containing various toxins with concentration of about 100 $\mu$g/ml. 50 ml of 50% suspension of various kinds of magneto-conductive particles is employed.

| Magneto-conductive particles | Toxins | Removed amount (%) |
| --- | --- | --- |
| Iron | low-molec.: | 90 |
| Carbon coated iron | barbiturate | 85 |
| Iron | med.-molec.: | 67 |
| Carbon coated iron | vitamin $B_{12}$ | 54 |
| Silicone coated iron |  | 75 |
| Iron | high-molec.: | 70 |
| Carbon coated iron | free hemoglobin | 60 |
| Protein, carbon coated iron |  | 90 |
| Dextran, carbon coated iron |  | 80 |

Those skilled in the art will readily appreciate that many modifications and changes may be applied to the invention as described in the preferred embodiment thereof without departing from its scope defined in and by the appended claims. For example, should the patient's lymph be corrected, the extracorporeal system is interconnected between the patient's large pectoral lymph duct and vein. In order to correct the spinal cord fluid the system is interconnected between two locations on the spinal cord channel.

What is claimed is:

1. A system for correcting a patient's biological fluid containing various low-, medium- and high-molecular toxins, the system comprising:
   (i) outlet means for attaching to a first location on a patient's body for substantially continuously withdrawing therefrom the biological fluid containing the various toxins;
   (ii) an extracorporeal flow line coupled to said outlet means for passing therethrough, in a substantially continuous flow, a predetermined substantially small amount of the biological fluid as compared to a whole amount of the biological fluid contained in the patient's body, so as to be mixed with a plurality of magneto-conductive particles capable of adsorbing said toxins for obtaining a mixture of the biological fluid with said particles;
   (iii) magnetic means comprising a magnetic field source for providing a magnetic field region within a flow of said mixture for retaining said magneto-conductive particles in said region from a flow of particle-free biological fluid, the magnetic field induction being within a range of 30–100 mTl, said magnetic means comprising a magnetic filler located inside the flow line within said magnetic field region, thereby increasing gradient and magnetic flux density of the magnetic field within said region;
   (iv) inlet means for attaching to a second location on the patient's body for returning the particle-free biological fluid back into the patient's body; and
   (v) control means coupled to the flow line and to the magnetic means for control thereof.

2. The system according to claim 1, wherein said flow line is in the form of a flexible tube.

3. The system according to claim 1, wherein said magneto-conductive particles are contained in a vessel coupled to the flow line through a pipe.

4. The system according to claim 3, and also comprising a feeding means for substantially continuously feeding the particles into and through the flow line.

5. The system according to claim 4, wherein said feeding means comprises a pump coupled to the vessel for supplying air thereto so as to provide an excessive pressure within the vessel.

6. The system according to claim 1, and also comprising a feeding means for substantially continuously feeding the biological fluid containing various toxins into and through the flow line.

7. The system according to claim 4, wherein said feeding means comprises a peristaltic pump.

8. The system according to claim 1, wherein the magneto-conductive particles are located inside the flow line in a flow path of the biological fluid containing the various toxins.

9. The system according to claim 8, wherein the flow line comprises first and second flexible tubes and a sealed vessel, the magneto-conductive particles being accommodated within the bottom region of the vessel, the first tube being connected between the outlet means and the particles, the second tube being connected between the inlet means and a top region of the vessel.

10. The system according to claim 1, wherein the particles are contained in a suspension thereof.

11. The system according to claim 10, wherein the suspension is formed of a blood substitute composition.

12. The system according to claim 10, wherein the suspension is formed of physiological solution or the like allowed for intravenous injection.

13. The system according to claim 1, wherein the biological fluid containing the various toxins is blood.

14. The system according to claim 13, wherein said first and second locations are associated with the patient's artery and vein, respectively.

15. The system according to claim 13, wherein said first and second locations are associated with the patient's vein.

16. The system according to claim 18, wherein said first and second locations are associated with a large pectoral lymph duct the patient's vein.

17. The system according to claim 19, wherein said first and second locations are associated with a spinal cord channel.

18. The system according to claim 1, wherein the biological fluid containing the various toxins is lymph.

19. The system according to claim 1, wherein the biological fluid containing various the various toxins is spinal cord fluid.

20. The system according to claim 1, wherein said substantially small amount of the withdrawn biological fluid at any given time is within the range 15–50 ml.

21. The system according to claim 1, wherein the magneto-conductive particles are formed of paramagnetic or ferromagnetic material.

22. The system according to claim 1, wherein the magneto-conductive particles are formed of hydrophilic material.

23. The system according to claim 1, wherein the magneto-conductive particles are formed of hydrophobic material.

24. The system according to claim 1, and also comprising a mixing means located in the flow path of the biological fluid containing the various toxins.

25. The system according to claim 24, wherein the mixing means comprises a multi-threaded worm mechanism.

26. The system according to claim 24, wherein the mixing means comprises a magnetic mechanism having displaceable opposite magnetic poles.

27. The system according to claim 1, wherein said magnetic filler serves as
adhering means for adhering thereon the magneto-conductive particles.

28. The system according to claim 27, wherein the magnetic filler a paramagnetic or ferromagnetic material.

29. The system according to claim 28, wherein the filler is in the form of a loosely laid wire.

30. The system according to claim 29, wherein said loosely laid wire is in the form of a barbed wire.

31. The system according to claim 30, wherein the wire has a varying diameter thereof and a varying laying density within the magnetic field region.

32. The system according to claim 27, wherein the magnetic field source and the adhering means are constituted by at least one permanent magnet accommodated inside the flow line.

33. The system according to claim 1, wherein the magnetic field source includes at least one permanent magnet mounted outside the flow line and proximate thereto.

34. The system according to claim 33, wherein said at least one permanent magnet is in the form of a substantially flat plate.

35. The system according to claim 33, wherein said at least one permanent magnet is ring-shaped for surrounding the flow line.

36. The system according to claim 33, wherein opposite poles of each magnet are connected by a cover plate formed of a magnetic soft material.

37. The system according to claim 1, wherein said control means includes:
a plurality of clamps accommodated along the flow line for regulating the flow of the biological fluid; and
a monitoring means for checking velocities of the flow of the biological fluid containing the various toxins, the mixture and the particle-free biological fluid.

38. The system according to claim 37, and also comprising a filtering means for removing water from blood.

39. The system according to claim 38, wherein the filtering means includes at least one semipermeable membrane.

40. The system according to claim 38, wherein the filtering means includes adsorbent material formed of hydrolyzed starch polymer.

41. The system according to claim 38, wherein said filtering means is accommodated in the flow path of the biological fluid containing the various toxins.

42. The system according to claim 38, wherein said filtering means is accommodated in the flow path of the particle-free biological fluid.

43. The system according to claim 1, wherein the magneto-conductive particles are formed with activated porous surfaces.

44. The system according to claim 43, wherein said particles are formed of iron.

45. The system according to claim 43, wherein said particles are formed of iron oxide.

46. The system according to claim 43, wherein said particles are formed of carbon coated iron.

47. The system according to claim 43, wherein said particles are formed of silicone coated iron.

48. The system according to claim 43, wherein said particles are formed of aluminum coated iron.

49. The system according to claim 43, wherein said particles are formed of dextran coated iron.

50. The system according to claim 43, wherein said magneto-conductive particles are coated with a protective layer formed of protein or the patient's blood.

51. A method of correcting a patient's biological fluid containing various low-, medium-, and high-molecular toxins, the method comprising the steps of:
(i) substantially continuously withdrawing the biological fluid containing various toxins from a patient's body into an extracorporeal flow line capable of passing therethrough a predetermined substantially small amount of the biological fluid as compared to a whole amount of the biological fluid contained in the patient's body;
(ii) mixing said predetermined substantially small amount of the biological fluid with a plurality of magneto-conductive particles capable of absorbing said toxins for obtaining a mixture of the biological fluid with said particles;
(iii) providing a magnetic field in a region within a flow path of the obtained mixture for retaining said magneto-conductive particles in said region from a flow of particle-free biological fluid, the magnetic field induction being within a range of 30–100 mTl; and
(iv) providing a magnetic filler within the magnetic field region for increasing gradient and magnetic flux density of the magnetic field within said region;
(v) returning the particle-free biological fluid back into the patient's body.

52. The method according to claim 51, wherein said step (ii) comprises: substantially continuously feeding the magneto-conductive particles from a vessel containing the same into the flow line.

53. The method according to claim 51, and also comprising filtration of the blood containing various toxins by removing water therefrom.

54. The method according to claim 51, and also comprising filtration of the particle-free blood by removing water therefrom.

55. A system for correcting a patient's biological fluid containing various low-, medium- and high-molecular toxins, the system comprising:
outlet means for attaching to a first location on a patient's body for substantially continuously withdrawing therefrom the biological fluid containing the various toxins;
an extracorporeal flow line coupled to said outlet means for passing therethrough, in a substantially continuous flow, a predetermined substantially small amount of the biological fluid as compared to a whole amount of the biological fluid contained in the patient's body, so as to be mixed with a plurality of magneto-conductive particles capable of adsorbing said toxins for obtaining a mixture of the biological fluid with said particles;

magnetic means comprising a magnetic field source for providing a magnetic field region within a flow of said mixture for retaining said magneto-conductive particles in said region from a flow of particle-free biological fluid, the magnetic field induction being within a range of 30–100 mTl, said magnetic means comprising a magnetic filler located inside the flow line within said magnetic field region, thereby increasing gradient and magnetic flux density of the magnetic field within said region;

inlet means for attaching to a second location on the patient's body for returning the particle-free biological fluid back into the patient's body;

control means coupled to the flow line and to the magnetic means for control thereof; and a filtering means for removing water from blood.

56. The system according to claim 55, wherein the filtering means includes at least one semipermeable membrane.

57. The system according to claim 55, wherein the filtering means includes adsorbent material formed of hydrolyzed starch polymer.

58. The system according to claim 55, wherein said filtering means is accommodated in the flow path of the biological fluid containing the various toxins.

59. The system according to claim 55, wherein said filtering means is accommodated in the flow path of the particle-free biological fluid.

* * * * *